(12) United States Patent
Nasser

(10) Patent No.: US 9,532,901 B2
(45) Date of Patent: Jan. 3, 2017

(54) FERTILITY PRESERVATION DEVICE

(71) Applicant: Nicola Nasser, Nazareth, IL (US)

(72) Inventor: Nicola Nasser, Nazareth, IL (US)

(73) Assignee: Mor Research Applications Ltd., Tel Aviv (IL)

( * ) Notice: Subject to any disclaimer, the term of this patent is extended or adjusted under 35 U.S.C. 154(b) by 188 days.

(21) Appl. No.: 13/759,521

(22) Filed: Feb. 5, 2013

(65) Prior Publication Data

US 2014/0216464 A1    Aug. 7, 2014

(51) Int. Cl.
*A41D 13/11*    (2006.01)
*A61F 7/12*    (2006.01)
*A61F 7/00*    (2006.01)
*A61F 7/02*    (2006.01)

(52) U.S. Cl.
CPC ............ *A61F 7/12* (2013.01); *A61F 2007/005* (2013.01); *A61F 2007/0056* (2013.01); *A61F 2007/0075* (2013.01); *A61F 2007/0287* (2013.01)

(58) Field of Classification Search
USPC .................. 128/830–833; 607/113–116, 138
See application file for complete search history.

(56) References Cited

U.S. PATENT DOCUMENTS

| | | | |
|---|---|---|---|
| 2,867,215 A | | 1/1959 | Horton et al. |
| 4,860,748 A | | 8/1989 | Chiurco et al. |
| 4,946,435 A | * | 8/1990 | Suthanthiran ............ A61K 9/70 600/1 |
| 5,242,428 A | * | 9/1993 | Palestrant ...................... 604/265 |
| 6,035,238 A | * | 3/2000 | Ingle .................. A61B 18/1485 607/101 |
| 6,139,569 A | | 10/2000 | Ingle et al. |
| 6,159,207 A | | 12/2000 | Yoon |
| 6,451,044 B1 | | 9/2002 | Naghavi et al. |
| 6,546,933 B1 | | 4/2003 | Yoon |
| 2003/0096406 A1 | | 5/2003 | Atala et al. |
| 2003/0215900 A1 | * | 11/2003 | Moses et al. ................... 435/23 |
| 2003/0216611 A1 | | 11/2003 | Q. Vu |
| 2005/0085880 A1 | | 4/2005 | Truckai et al. |
| 2007/0225781 A1 | * | 9/2007 | Saadat ...................... A61F 7/12 607/105 |
| 2009/0149797 A1 | | 6/2009 | Dacey, Jr. et al. |
| 2011/0264075 A1 | | 10/2011 | Leung et al. |

FOREIGN PATENT DOCUMENTS

WO    02/00145 A1    1/2002
WO    2007/109656 A2    9/2007

OTHER PUBLICATIONS

International Search Report for International Application No. PCT/IB2011/053447, mailed Mar. 29, 2012.
KD Hopper, JD Neuman; SH King; AR Kunselman. Radioprotection to the eye during CT scanning. Jun./Jul. 2001. AJNR Am J Neuroradiol 22:1194-1198.

* cited by examiner

*Primary Examiner* — Ophelia A Hawthorne
(74) *Attorney, Agent, or Firm* — Marsteller & Associates, P.C.

(57) ABSTRACT

The invention relates to ovary apparatus for regulating the temperature of the ovary; and shielding it from radiation. The main function of the device is to preserve fertility of women treated with chemotherapy by lowering the ovary temperature while the toxic medications circulate in the patients' blood. The current invention utilizes shielding of the ovary to protect it from radiation, and temperature decrease to further limit the toxic effect of radiation.

20 Claims, 2 Drawing Sheets

Fig. 3
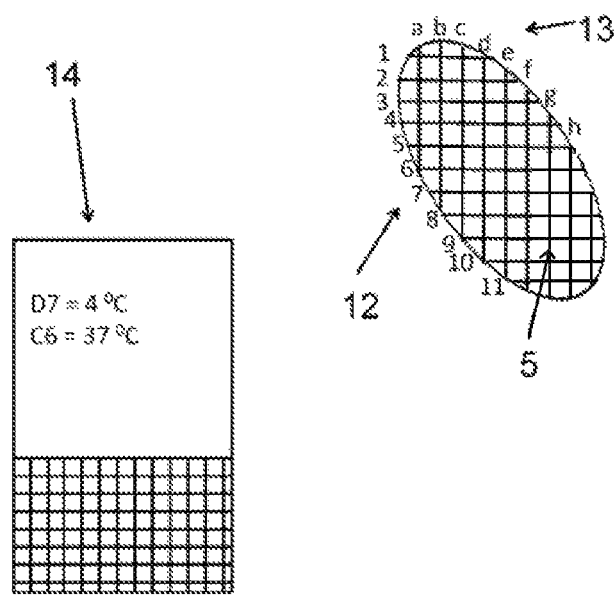
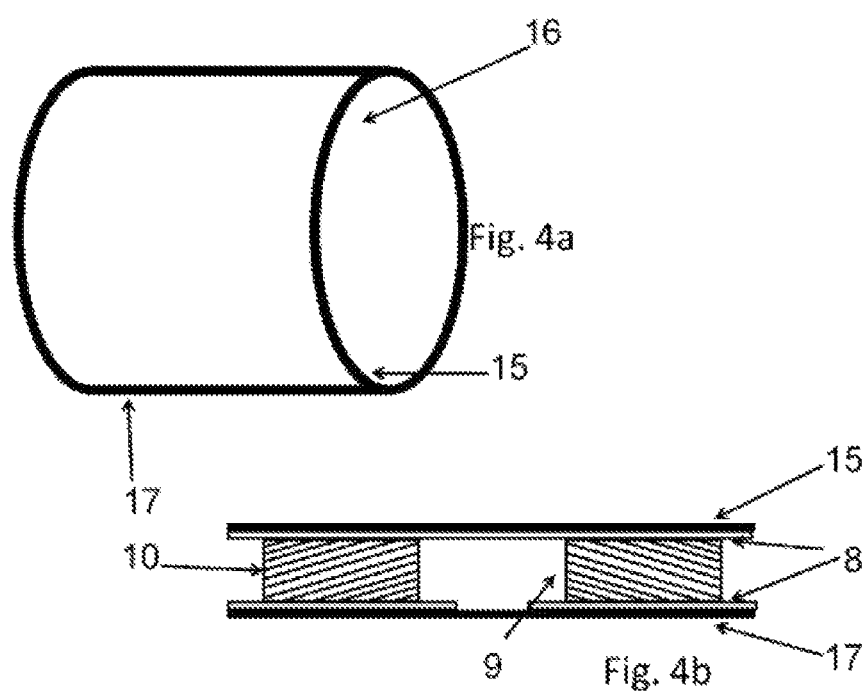
Fig. 4a
Fig. 4b

FERTILITY PRESERVATION DEVICE

FIELD OF THE INVENTION

The present invention relates to a medical device that modulates the ovary temperature, in order to modulate its function, and preserve fertility, especially of women who suffer from cancer and receive treatments that jeopardize fertility such as chemotherapy.

BACKGROUND OF THE INVENTION

Fertility is the ability of a person to make children through mating with a person from the other sex. The ovaries in women and the testicles in men are vital organs to fertility in women and men, respectively. Ovaries and testicles (gonads) contain 'gametes' which are haploid cells (gametes contain half of the set of chromosomes found in the other human cells). The ovarian gametes are called 'ova', and the testicular gametes are called 'sperm'. Healthy men are usually able to produce sperm from adolescence till late adulthood; conversely women are born with about 100,000 ova per ovary and with age this number decreases steadily; by puberty only about 30,000 ova per ovary survive, and from puberty till menopause only 300-400 ova ripens. Beside production of gametes, the gonads have vital functions related to hormonal production such as estrogen, progesterone and testosterone secretion which affects many organs in the body and changes in these hormones can result in a variety of problems such as libido disturbances, mood disorders, cardiovascular disease and bone density disturbances (osteoporosis). Moreover, suppression of the hormonal production in the gonads is utilized in treatment of cancer diseases: Castration (either surgical or chemical) is widely used to treat metastatic and locally advanced prostate cancer; and ovarian suppression is used to treat breast cancer patients suffering from tumors expressing estrogen or progesterone receptors. Gonadal function preservation and/or function modulation are needed in the following settings:

Fertility preservation in patients treated due to cancer disease.
  a. Women. Cancer is the second cause of death in western countries. One out of ten women, on average, suffers from breast cancer. In 2008, approximately 182,000 women in the United States were expected to receive a diagnosis of invasive breast cancer, of these patients, an estimated 16,000 were younger than 45 years of age (1). 'Chemotherapeutic agents routinely used for the treatment of breast cancer include cyclophosphamide, fluorouracil, doxorubicin, pa-clitaxel, and docetaxel. Alkylating agents, including cyclophosphamide, are quite toxic to the ovaries, particularly to the primordial follicles, which represent the ovarian reserve. Although the effect of chemotherapeutic regimes on fertility is predicated or the baseline ovarian reserve, treatment effects become particularly pronounced by the time patients reach 40 years of age.' (1). As detailed in a recent review in the New England Journal of Medicine (1) 'Several options are available to women with cancer who wish to preserve their germline. Patients may elect to delay cancer treatment in order to undergo one cycle of hormone stimulation, followed by cryopreservation of either a mature oocyte or an embryo. Both techniques require a delay in cancer treatment for up to 1 month; this may not be an option for some patients. Cryopreservation of mature oocytes is considered experimental, although more than 100 live births have been reported with the use of this technique,' (1) 'Fertility-preservation techniques that do not require hormonal exposure are available. Ovarian tissue can be obtained at the time of diagnosis without additional hormonal stimulation, thus only minimally interfering with the patient's treatment plan. Depending on the day of the menstrual cycle, oocytes may be aspirated from the ovary, matured in vitro, and then cryopreserved for later use. In addition, individual follicles or strips of ovarian cortical tissue can be cryopreserved directly for future use in either in vitro follicle maturation or tissue transplantation. Thus far, five live births have been reported in women with cancer who underwent autologous transplantation of cryopreserved ovarian tissue.' (1)
  b. Men. Men undergoing chemotherapeutic treatments and wish to preserve their fertility undergo usually sperm banking. When the patient and his spouse wish, the spouse undergoes insemination or in vitro fertilization. This method, although effective, do not preserves the natural fertility of the man, and these patients may suffer from chemotherapy induced oligospermia, which complicates the conception process. Moreover, if the banked sperm get lost or defective the patient's options for parenthood decrease.
  e. Children. In the United States, 10,700 new cases of cancers were diagnosed in children in 2008 (1, 2). Of these patients, nearly 80% were expected to survive (2). Treatment regimens for childhood cancers are extremely toxic and pose a threat to the fertility of young patients (1). The current options for fertility preservation are limited in their effectiveness in both girls and boys (especially those before adolescence).
2. Women with hereditary genetic mutations in genes such as BRCA-1 and BRCA-2 are at increased risk for ovarian cancer. The current practice is to perform ovarian resection as early as possible to these women, preferably before the age of 25-30 years, before the development of cancer. Clearly, resection of the ovaries at young age results in compromise of the fertility in these women, as well as induces early menopause. Currently, there is no method to prevent or delay cancer development in ovaries of women with genetic mutations posing them at increased risk of ovarian malignancies.
3. Broadening the 'fertility window'. As stated above, fertility of healthy women decreases with age. Above age 30-35 years it becomes more difficult for women to get pregnant. In the last century more and more women arrive to this age without children due to either career related issues or due to lack of appropriate spouse. These women seek methods to broaden the 'time window' of pregnancy beyond the age of 40 or 50 years. Currently, there is no solution for healthy women to broaden the fertility window.
4. Delaying menopause. By the age of 50 years most women arrive to menopause. Menopause results from lack of ovarian functionality, not solely lack of ovulation, but also lack of production of sex hormones (e.g. estrogen and progesterone). Beside its effect on fertility, the hormonal changes at menopause results in changes in almost every organ. Lack of estrogen results in faster aging, more heart diseases (atherosclerosis), and bone density changes (osteoporosis). Women beyond the age of menopause can use hormone replacement therapy to compensate for the hormonal changes that ovarian failure causes by menopause, and lower the development of osteoporosis, coronary heart disease, and changes to the skin texture.

5. Birth control. Family planning and pregnancy timing are widely used in the last decades by women. There are a variety of birth control methods available for women. This includes birth control pills, intrauterine device and a variety of mechanical barriers.
6. Polycystic Ovary Syndrome Polycystic ovary syndrome is one of the most common female endocrine disorders, affecting approximately 5%-10% of women of reproductive age (12-45 years old) and is thought to be one of the leading causes of female subfertility (6). Medical treatments of women with infertility due to polycystic ovary syndrome rely mainly on medications such as clomiphene citrate. Surgical treatment of infertility due to polycystic ovary syndrome include either 'wedge resection' of one ovary, or 'ovarian drilling' which can be done laparoscopically by making small holes in the ovarian coating or capsule with a laser or cautery needle. Ovarian wedge resection and ovarian drilling results in induction of ovulation in women suffering from polycystic ovary syndrome for a limited number of months after the procedure, providing the opportunity to these patients to get pregnant.
7. Treatment of breast cancer patients with ovarian suppression. Ovarian suppression, with the use of gonadotropin-releasing hormone analogues, plus tamoxifen is a standard adjuvant treatment in premenopausal women with endocrine-responsive breast cancer (8). Resection of the ovaries, is another alternative to ovarian suppression with long acting gonadotropin-releasing hormone analogues, but is usually reserved for women with hereditary breast and ovary genes mutations.

Use of Hypothermia to Protect Tissues and Organs from Chemotherapy.

Changes in temperature are used in limited situations in cancer patients to decrease exposure to chemotherapeutic drugs, and thus preserve the organ function:
1. Prevention of Chemotherapy-Induced Hair Loss with Scalp Hypothermia: Treatment of patients who suffer from cancer includes the administration of chemotherapeutic drugs such as doxorubicin and cyclophosaphamide which induce hair loss, alopecia, in many cases. Prevention of doxorubicin-induced hair loss with scalp hypothermia was reported in many controlled trails as early as the report in the New England Journal of Medicine in 1979 (4), Satterwhite et al. showed that scalp hypothermia resulted in preservation of hair in 75% of patients treated with doxorubicin as compared with 8% in the control group (5). The mechanism by which cooling results in preservation of hair is not well characterized, but is thought to be a combination of decreased exposure to chemotherapy during the cooling period, and decrease in the hair follicle metabolic rate, which culminates in resistance to chemotherapy. Because chemotherapy disturbs the normal metabolizing cell, cooling the cell, decreases its metabolism and puts a significant part of its functions 'on-hold' rending chemotherapy less active.
2. Hypothermia gloves are frozen gloves that the patient wears in order to protect fingers and nails from the side effects of chemotherapy (3). Onycholysis and skin toxicity occur in approximately 30% of patients treated with docetaxel. A multicenter study by Florian Scotté et al. (7) showed that frozen glove significantly reduces the nail and skin toxicity associated with docetaxel and provides a new tool in supportive care management to improve patient's quality of life. In this study, patients receiving docetaxel 75 mg/m² alone or in combination with other chemotherapy were eligible for this case-control study. Each patient wore a frozen glove for a total of 90 minutes on the right hand. Onycholysis and skin toxicity were significantly lower in the frozen glove-protected hand compared with the control hand (P=0.0001). Onycholysis was grade (G) 0 in 89% v 49% and G1 to 2 in 11% v 51% for the frozen glove-protected hand and the control hand, respectively. Skin toxicity was G0 in 73% v 41% and G1 to 2 in 27% v 59% for the frozen glove-protected and the control hand, respectively (7).

SUMMARY OF INVENTION

The present invention relates to ovary apparatus for regulating the temperature of the ovary. The use of cytotoxic agents, for example, chemotherapy for cancer patients leads to injury to ovarian cells and reduce fertility. The current invention utilizes temperature changes in order to modulate function, or to preserve function of the ovary. The normal body temperature is 37° C., by decreasing the temperature of the ovary (while it inside the body connected to its normal blood and nerve supply) the current invention results in decrease in the ovary metabolic rate, change the blood flow to the ovary and decrease the ovary sensitivity to toxic materials such as chemotherapy. The current invention is designed to selectively change the temperature of the ovary or past of it without changing of the temperature of the whole body. The preferred embodiment is to decrease the temperature of the ovary to less than 37° C. for varying time periods in order to modulate its function or preserve its function. The preferred embodiment is related to decreasing the ovary temperature in order to preserve its function during cancer treatment or to extend its functionality period in healthy people. Other embodiments are selective increase of the temperature of part of the ovary in order to induce 'wedge resection' of the ovary and hence induce ovulation in women suffering from polycycstic ovary syndrome. Other uses for ovarian temperature modulation device of the current invention, include: modulation of hormone secretion from the ovaries through ovarian cooling; decrease in the metabolic rate of the ovaries thought decreasing ovarian temperature below 37° C. in order to prevent development of breast and ovary malignancies in young women with genetic mutations posing them to ovarian and breast carcinomas; birth control; delaying menopause; protecting the ovary from radiation induced damage by modulating the temperature of the ovary, decreasing its metabolic rate, and decreasing free radical production in the ovaries by radiation through ovarian cooling. Another embodiment of the invention is an ovary shielding device (FIG. 2), the external walls of the device built from radiation shielding materials such as lead, with a possibility to control its internal cavity temperature, which contains the ovary, in order to further decrease the harm from radiation to the ovary.

The fertility preservation device is an implantable device, in one embodiment it functions as a small cooling machine, in which the cooling part encases and covers the ovary like a glove cover the hand; or, in other embodiment, an intra arterial cooling stent inserted into the ovarian arteries cool the blood supply to the ovary and thus results in reducing the temperature of the ovary. The device may be inserted through a bed-side gynecologic procedure in which the device introduced through the vagina to the uterus to the fallopian tubes and from there to the ovary. Alternatively the device may be implanted through laparoscopic or open surgical procedures. Alternatively, in the case of an intravascular cooling stent the device may be inserted through angiographic procedures. The energy supply can be from a battery that can be recharged from outside the body, or through an external electric source, or from transforming the body temperature or the movement of its organ to an electric power that supplies the energy needed for this device. The temperature level and length of the temperature changes will be modulated according to the goal of the treatment (see 'Background of the Invention'). The range of temperature is between −20° C. to 100° C., and the cooling period range is from minutes to years. For preserving fertility in women treated with medications that affect fertility (e.g. chemotherapy) the length of ovarian temperature modulation will be set till the concentration of the medication in the blood decrease below its expected gonado-toxic level (this may also be calculated according to the expected half-life of the medication). The return of the temperature of the ovaries to the normal body temperature may be abrupt or gradual, according to the clinical needs. By decreasing ovarian temperature this invention will decrease the metabolic function of the gonads cells and thus protect them from the cytotoxic effect of drugs such as chemotherapy and front exposure to radiation therapy harms. The current invention, temperature modulation device that covers the ovaries, can be produced from or covered by radiation protecting materials such as lead, in order to further protect the gonads from radiation.

Other uses of the invention related to gonadal and ovarian function modulation, include decreasing the temperature of one ovary or both ovaries in order to extend 'fertility window', delay menopause, delay menarche, induce menarche, or induce menopause. The current invention can be used to suppress gonadal hormonal function through modulation of ovarian temperature; preferably cooling the gonads will result in hormonal suppression which can be used for treating hormone sensitive malignancies such as hormone receptor positive breast cancer. Extending the fertility window may be achieved by cooling one ovary for long period, and following the menopausal status of the woman; when the on-cooled ovary stop functioning and the woman approaches menopause, then the temperature of the cooled ovary is returned to normal body temperature or near body temperature, in order to allow fertility beyond menopause. As there is relation between hormonal function and aging, this device can be used for modulating the temperature of ovaries in order to delay aging. For example, temporary cooling of one ovary by using the current invention, can result in preserving ovarian function 'beyond menopause', which results in longer pre-menopausal life, and less aging.

The current invention can be used as a birth control method through modulation of ovarian temperature.

DESCRIPTION OF DRAWINGS

FIG. 3 shows an embodiment of the apparatus for regulating the temperature of the ovary 5, composed of cells, in which the temperature of each cell can be controlled individually. Each cell is designated fey horizontal number 12, and vertical letter 13, and utilizing a remote control 14, the temperature of each cell is set from outside the body of the patient while the device is already implanted and encases the ovary.

FIGS. 4*a*-4*b* show an embodiment of the apparatus for regulating the temperature of the ovary in the shape of vascular stent. FIG. 4*a* the cooling stent is shown in its open format 16, the cooling surface of the apparatus is forming the internal wall of the stent 15, while the external wall of the stent is made from insulating material and faces the blood vessel endothelium, 17. FIG. 4*b* is an enlarged schematic description of the stent wall composed of external layer made from insulator material 17, conductor 8, n-type thermo-element 9, p-type thermo-element 10, and direct current source (not shown).

DETAILED DESCRIPTION OF THE INVENTION

In accordance with the invention, the toxic effects of chemotherapy on ovarian function in premenopausal women treated due to cancer could be reduced by decreasing the temperature of the ovary during treatment. The ovary is a small oval organ with dimensions of about 1.5 cm×3 cm; the current invention is an implantable device, which modulate the temperature of the ovary. By reducing the temperature of the ovary, the metabolic rate of ovarian cells decrease, energy consumption of the ovarian cells decrease, and blood flow to the ovary change. This change due to lowering of the ovary temperature decreases the vulnerability of ovarian cells to chemotherapy, similar to the decreased hair loss from scalp cooling, and the lower toxicity to the nails when using freezing gloves during chemotherapy treatments.

In another aspect of the invention, sufficient decrease in the temperature of the ovaries by the current invention will result in decreased hormonal secretion from the ovaries, which can be utilized to treat breast cancer malignancies in premenopausal women with endocrine-responsive breast cancer.

Figure 1:
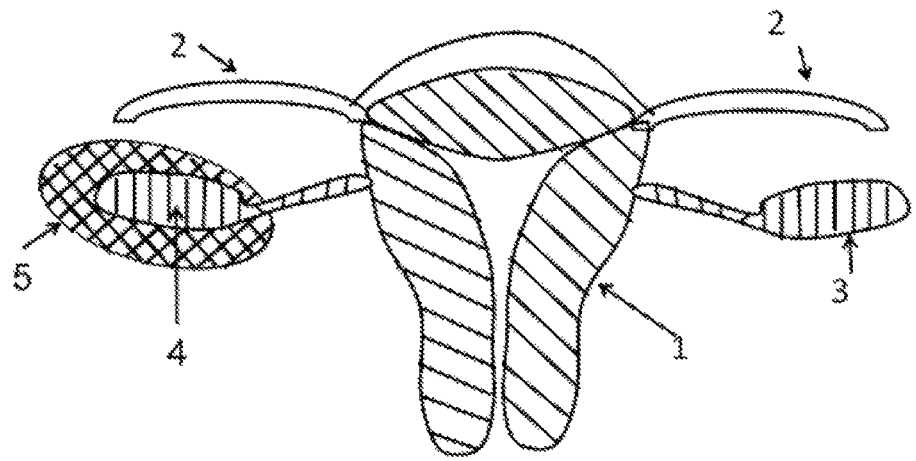
FIG. 1 shows a schematic view of the women uterus 1, fallopian tubes 2 and ovaries (3 & 4) and the ovarian apparatus for regulating the temperature of the ovary and shielding it from radiation 5 covering the right ovary 4.
Figure 2:
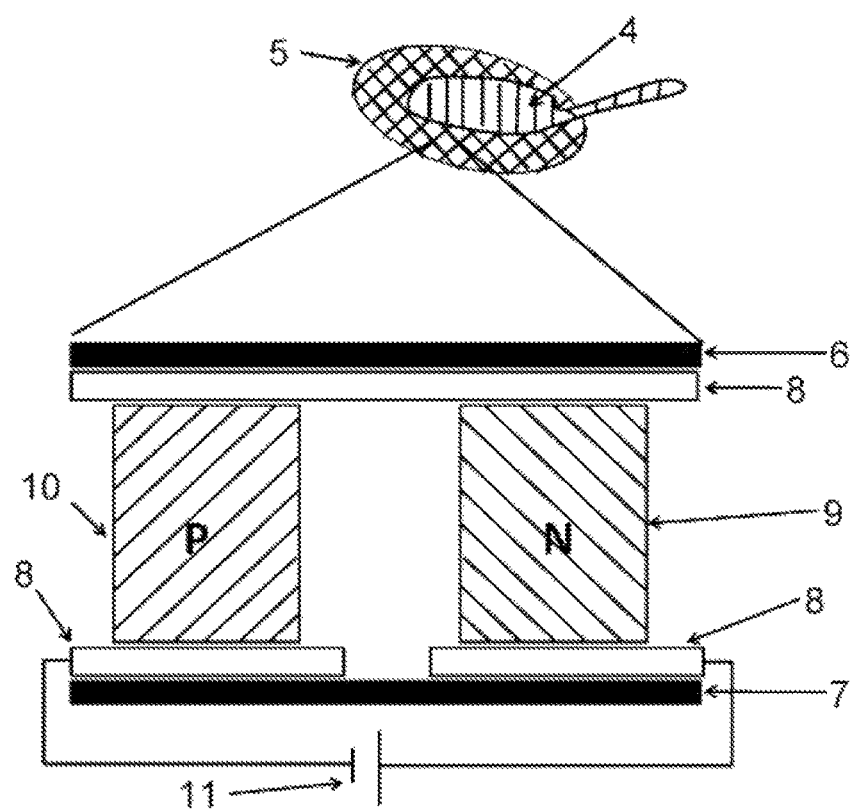
FIG. 2 shows one embodiment of the apparatus for regulating the temperature of the ovary utilizing the thermoelectric effect. The ovary 4 is encased by the temperature regulating apparatus 5. Enlarged inset of one embodiment of the ovarian temperature regulating apparatus is composed of an internal layer and an external layer. The internal layer 6 is lining the apparatus and contacting the ovary 4. The external layer is made from an insulator material and a radiation shielding material such as lead 7. The external layer is composed of a conductor 8, an n-type thermo-element 9, a p-type thermo-element 10, and a direct current source 11.

In yet another aspect of the invention, and in order to further protect fertility of women suffering from cancer treated with radiation, an implantable ovarian cooling device of the current invention, shaped in shell-like form (FIG. 1), or covers the ovary like a glove cover the hand (in one embodiment), with its external wall built from materials that function as a shield for the ovary from radiation (FIG. 2), such as lead or any other radiation shielding material, in order to physically decease the gonads exposure to radiation, and assist in visualizing the location of the gonads during radiation therapy simulation, and before each radiation session treatment in order to treat the patient with image guided radiation therapy (IGRT) technique, and lower the total radiation dose that the ovary receive during radiation of abdominal or pelvic tumors. Lowering the temperature of the ovary during radiation therapy reduces its metabolic rate, decrease free radicals production, and makes the ovary less vulnerable to radiation.

In yet another aspect of the invention, the medical device of the current invention lowers the temperature of the ovary, which results in lowering its metabolic rate. Prolonged moderate-cooling of the ovary can prevent aging of ovarian cells, and delay menopause by a time equivalent to the cooling period of one of the ovaries. For example, if cooling of the right ovary was initiated when the woman was 35 years old, for 15 years, then after cooling stops at age 50, the right ovary will be more active than the left un-cooled ovary, which results in delaying the menopause of the treated woman.

In one embodiment, the ovarian-temperature-modulating-device has a shell-like shape (FIG. 1), or glove-like shape that covers the ovary and contains it, and modulates its temperature. In this embodiment, the temperature of the ovarian cortex can be highly controlled. In this embodiment, the ovarian cortex comes into close contact with the interior side of the medical device described in the current invention. The temperature of the ovarian cortex in this embodiment can be homogenously or differentially modulated. In the embodiment that deferentially modulates the ovarian surface cortex (FIG. 3), temperature differences between the different areas of ovarian cortex can be obtained by matrix-like-device which is divided into cells in which the temperature of each cell can be controlled. The matrix covers the ovary, and comes into close contact with the ovarian cortex, and hence the temperature of each part of the ovarian cortex can then be controlled by changing the temperature of the different matrix cells. Each square millimeter of ovarian cortex, surface can be cooled or heated to different temperature, allowing temperature differences between the different areas of ovarian cortex. Differential temperatures of the ovarian cortex, can be used to treat women with poly cystic ovary syndrome, in order to induce wedge-resection-like local injury to the ovary, or ovarian-drilling like injury to the ovarian cortex. In this example, one or two millimeters of ovarian cortex are heated to 75-100° C. for 15 minutes, while the ovarian cortex that borders this area is maintained at 20-37° C. This differential temperature modulation will result in controlled injury to the ovarian surface, and induce ovulation in patients with polycystic ovary disease. Given the possibility that this device can be remotely controlled (FIG. 3), each time the women desire to ovulate, an increase in the temperature of small part of the ovary is performed in order to induce 'wedge like' temperature induced destruction. If the women desire to repeat the procedure in the future, then another part of the ovary will be chose in order to induce wedge resection.

In another embodiment, ovarian-temperature-modulating-device of the current invention has a stem-like shape (FIGS. 4a-4b), inserted through angiographic procedure into the blood vessel that supply the ovary, and cool the blood that arrives to the ovary, resulting in reduction of the temperature, of the whole ovary.

In another embodiment, the current ovarian-temperature-modulating-device can be utilized for prevention of cancer development in ovaries of women with genetic mutations posing them at increased risk of ovarian malignancies. Women with hereditary genetic mutations like BRCA-1 and BRCA-2 gene mutations are at increased risk for ovarian cancer. Through the current invention a decrease of the ovarian temperature in these women will decrease the metabolic rate in the ovaries, and decrease the possibility for development of cancer in the cooled ovaries. Moreover, reducing the temperature of the ovaries in these gene mutation carriers will result in decrease in estrogen and progesterone secretion torn the ovaries, which will result in beneficial consequences in terms of lowering the probability to developing breast cancer in these patients.

In one embodiment of the invention, Peltier effect is used to create a heat flux between junctions of two different materials. As detailed in FIG. 2, the ovary 4, is covered by ovarian fertility device of the current invention 5. The wall of this device is composed from several layers 6-9, an internal layer lining the apparatus and contacting the ovary 6, external layer made from insulator material and radiation shielding material such as lead 7, conductor 8, n-type thermo-element 9, p-type thermo-element 10, and direct current source 11. The device can be inserted (FIG. 1) by invasive procedure, or by non-invasive procedure, through the uterus 1, fallopian tubes 2, and then stretched over the ovary 4. The device can be applied to one ovary 4, as in FIG. 1, leaving the other ovary 3 in its natural ambient, or two devices can be applied, each to one ovary (not shown). While thermoelectric effect is described here as an example to reduce or increase temperature, other methods such as utilizing coolant liquids, or methods utilized to cool electronic chips, laser lamps, or simple refrigerators could be utilized as well to achieve the goal of the current invention of modulating the ovary temperature.

While the apparatus described herein utilizes temperature changes in order to modulate ovarian functions, it's clear that the same methodology could be used to modulate the function of other internal organs through increase or decrease of temperature such as modulation of the temperature of the pancreas to treat diabetes, or to modulate the temperature of the pancreas for modulating its hormonal function. Moreover, the same device can be used to modulate the temperature of un-resectable tumors, such as pancreatic tumors, in order to disturb tumor cells metabolic rate by either reducing or increasing the tumor temperature from 37° C. and thus extend life and quality of life of patients.

While the invention was described with respect to limited number of embodiments, it will be appreciated that many variations, modifications and other applications of the invention may be made.

REFERENCES

1. Jeruss J S, Woodruff T K. Preservation of fertility in patients with cancer. N Engl J Med. 360: 902-911 (2009).
2. Cancer facts & figures 2008. Atlanta: American Cancer Society, 2008.
3. http://www.fordmedical.co.uk/id14.html
4. Prevention of Doxorubicin-Induced Hair Loss with Scalp Hypothermia, Judith C. Dean, R.N., M. S., Sydney E, Salmon, M.D., and Katherine S, Griffith, R.N. N Engl, J Med 1979; 301:1.427-1429
5. The use of scalp hypothermia in the prevention of doxorubicin-induced hair loss, Satterwhite B, Zimm S, Cancer, 1984; 54(1);34-7,
6. Polycystic ovary syndrome. Wikipedia, the free encyclopedia http:/en.wikipedia.org./wiki/Polycystic_ovary_syndrome (approached Jul. 30, 2011).
7. Multicenter Study of a Frozen Glove to Prevent Docetaxel-Induced Onycholysis and Cutaneous Toxicity of the Hand. Florian Scotté et al. *Journal of Clinical Oncology*, Vol 23, No 19 (July 1), 2005: pp. 4424-4429.
8. Endocrine Therapy plus Zoledronic Acid in Premenopausal Breast Cancer. Michael Gnant et. al. N Engl J Med 2009; 360:679-691.

The invention claimed is:
1. An implantable medical device for modulating function of an ovary, comprising:
  a) a flexible hollow element having a closed three-dimensionally curved surface and being provided with temperature regulating apparatus, said hollow element being implantable in such a way so as to enclose an ovary while an interior side of said hollow element is in heat exchanger relation with a cortex of said ovary;

b) an energy supply for powering, or inducing operation of, said temperature regulating apparatus; and, c) a controller for selectively controlling operation of said temperature regulating apparatus in order to modulate the function of said ovary in a desired way, wherein said temperature regulating apparatus comprises a non-linear matrix of cells that are spatially arranged along said curved surface, for differentially and controllably modulating the temperature of each cell to allow temperature differences between different areas of the cortex, each of said cells being operable to selectively reduce the temperature of said ovary or a portion thereof below a physiological body temperature in order to modulate function of said ovary without changing body temperature at a different body portion, wherein said controller continues operation of one or more of the cells until bloodstream concentration of fertility affecting medication being administrated decreases below an expected gonado-toxic level.

2. The medical device according to claim a 1 wherein the temperature regulating apparatus is also configured to controllably increase a portion of the ovary above the physiological body temperature.

3. The medical device according to claim 2, wherein the controller is operable to activate a first group of the cells so that a corresponding first portion of the cortex of the ovary is heated above the physiological body temperature and to activate a second group of the cells so that a corresponding second portion of the cortex bordering said first portion is maintained at a temperature less than or equal to the physiological body temperature.

4. The medical device according to claim 3, wherein the first group and second groups of the cells are activatable at different times.

5. The medical device according to claim 3, wherein the controller is operable to activate the first group of the cells so that one or two millimeters of an ovarian cortex is heated to a temperature ranging from 75 to 100° C. for approximately 15 minutes and to activate the second group of the cells so that a corresponding second portion of the ovarian cortex bordering said first portion is maintained at a temperature ranging from 20 to 37° C. in order to induce ovulation in patients suffering from a polycystic ovary syndrome.

6. The medical device according to claim 3, further comprising a remote control device in communication with the controller for selecting the first and second portions of the cortex.

7. The medical device according to claim 1, wherein the hollow element has a shell shaped or a glove shaped configuration.

8. The medical device according to claim 7, wherein the hollow element is made from radiation shielding material in order to decrease exposure to radiation while reducing a metabolic rate of the ovary due to operation of the temperature regulating apparatus.

9. The medical device according to claim 1, wherein the interior side of the hollow element is configured to be in contact with the cortex of the ovary.

10. The medical device according to claim 1, wherein the temperature regulating apparatus is operable to homogeneously cool the ovary.

11. The medical device according to claim 1, wherein the energy supply is selected from the group consisting of a fluid supply device, a battery that is rechargeable from outside a body in which the hollow element is implanted, a battery that is rechargeable by an external electric source, a power source disposed externally from the body, and auto-recharge means utilizing body induced energy.

12. A method for modulating function of an internal organ, comprising the steps of:

a) implanting within a patient a flexible hollow element having a closed three-dimensionally curved surface and being provided with temperature regulating apparatus, wherein the temperature regulating apparatus comprises a non-linear matrix of cells that are spatially arranged along said curved surface and are individually activatable, the method further comprising the following steps that are performed after implanting said hollow element;

b) positioning said hollow element in such a way so as to enclose an internal organ while an interior side of said hollow element is in heat exchanger relation with a cortex of said internal organ; and c) controllably and differentially powering said plurality of cells to selectively reduce a temperature of said internal organ or a portion thereof below a physiological body temperature in order to modulate function of said internal organ without changing body temperature at a different body portion.

13. The method according to claim 12, wherein the internal organ is an ovary and the hollow element is implanted by a laparoscopic or open surgical procedure, or by being introduced through a vagina to a uterus and then to fallopian tubes and an ovary during a bed-side gynecologic procedure.

14. The method according to claim 13, wherein one or more of the plurality of cells is operable to increase the temperature of the ovary or a portion thereof above the physiological body temperature, the method further comprising the step of controllably and differentially powering the plurality of cells so that a corresponding first portion of the cortex is heated above the physiological body temperature and a corresponding second portion of the cortex bordering said first portion is maintained at a temperature less than or equal to the physiological body temperature, whereby to induce local controlled thermal injury to the ovary and to induce ovulation.

15. The method according to claim 12, wherein the internal organ is an ovary and the modulated ovarian function is selected from the group consisting of hormonal suppression in order to treat hormone sensitive malignancies including hormone receptor positive breast cancer, decrease in metabolic rate of the ovary to prevent development of breast and ovary malignancies in women with genetic mutations posing them with an increased risk to ovarian and breast carcinomas, decrease in ovarian sensitivity to toxic materials, decrease in metabolic rate in order to provide protection from the cytotoxic effect of drugs and from exposure to radiation therapy damage, modulated hormone secretion from the ovary, birth control, delaying menopause, decrease in free radical production in the ovary by radiation, decrease in harm to the ovary from radiation as a result of a controlled internal cavity temperature, preserving fertility, extending a fertility window, delay in menarche, inducing menarche, inducing menopause, decrease in hormonal secretion from the ovaries in order to treat breast cancer malignancies in premenopausal women suffering from endrocrine-responsive breast cancer or to lower the probability in developing breast cancer, and delaying aging.

16. An implantable medical device for modulating function of an ovary, comprising a flexible hollow element having a closed three-dimensionally curved surface and being provided with temperature regulating apparatus, and an energy supply for powering, or inducing operation of, said temperature regulating apparatus, said hollow element being implantable in such a way so as to enclose an ovary while an interior side of said hollow element is in heat exchanger relation with a cortex of said ovary, wherein said temperature regulating apparatus comprises a non-linear matrix of cells that are spatially arranged along said curved surface, for differentially and controllably modulating the temperature of each cell to allow temperature differences between different areas of the cortex, each of said cells being operable to selectively reduce the temperature of said ovary or a portion thereof below a physiological body temperature in order to modulate function of said ovary without changing body temperature at a different body portion, wherein the modulated ovarian function is selected from the group consisting of hormonal suppression in order to treat hormone sensitive malignancies including hormone receptor positive breast cancer, decrease in metabolic rate of the ovary to prevent development of breast and ovary malignancies in women with genetic mutations posing them with an increased risk to ovarian and breast carcinomas, decrease in ovarian sensitivity to toxic materials, decrease in metabolic rate in order to provide protection from a cytotoxic effect of drugs and from exposure to radiation therapy damage, modulated hormone secretion from the ovary, birth control, delaying menopause, decrease in free radical production in the ovary by radiation, decrease in harm to the ovary from radiation as a result of a controlled internal cavity temperature, preserving fertility, extending a fertility window, delay in menarche, inducing menarche, inducing menopause, decrease in hormonal secretion from the ovaries in order to treat breast cancer malignancies in premenopausal women suffering from endocrine-responsive breast cancer or to lower the probability in developing breast cancer, and delaying aging.

17. The medical device according to claim 16, wherein the temperature regulating apparatus is also configured to controllably increase a portion of the ovary above the physiological body temperature.

18. An implantable medical device for modulating function of an internal organ, comprising a flexible hollow element having a closed three-dimensionally curved surface and being provided with temperature regulating apparatus, and an energy supply for powering, or inducing operation of, said temperature regulating apparatus, said hollow element being implantable in such a way so as to enclose an internal organ while an interior side of said hollow element is in heat exchanger relation with a cortex of said internal organ, wherein said temperature regulating apparatus comprises a non-linear matrix of cells that are spatially arranged along said curved surface, for differentially and controllably modulating the temperature of each cell to allow temperature differences between different areas of the cortex, each of said cells being operable to selectively reduce the temperature of said internal organ or a portion thereof below a physiological body temperature in order to modulate function of said internal organ without changing body temperature at a different body portion, wherein the interior side of said hollow element is configured to be in continuous contact with the cortex of said internal organ.

19. The medical device according to claim 18, wherein the temperature regulating apparatus is also configured to controllably increase a portion of the internal organ above the physiological body temperature.

20. A method for modulating function of an ovary, comprising the steps of:
a) implanting within a female patient a flexible hollow element being a matrix shaped device which is divided into a plurality of cells and provided with a plurality of cooling elements and a plurality of heating elements, the method further comprising the following steps that are performed after implanting said matrix shaped device:
b) positioning said matrix shaped device in such a way so as to enclose an ovary while an interior side of said matrix shaped device is in heat exchanger relation with a cortex of said ovary; and
c) controllably and differentially powering said plurality of cooling elements and said plurality of heating elements so that a corresponding first portion of the ovarian cortex is heated above a physiological body temperature and a corresponding second portion of the ovarian cortex bordering said first portion is maintained at a temperature less than or equal to the physiological body temperature, whereby to induce local controlled thermal injury to said ovary and to induce ovulation without changing body temperature at a different body portion, wherein said matrix shaped device is implanted by a laparoscopic or open surgical procedure, or by being introduced through a vagina to a uterus and then to fallopian tubes and an ovary during a bed-side gynecologic procedure.

* * * * *